Dec. 23 , 1952 L. L. BROOKS Plant Pat. 1,157
AZALEA PLANT
Filed Jan. 28, 1952
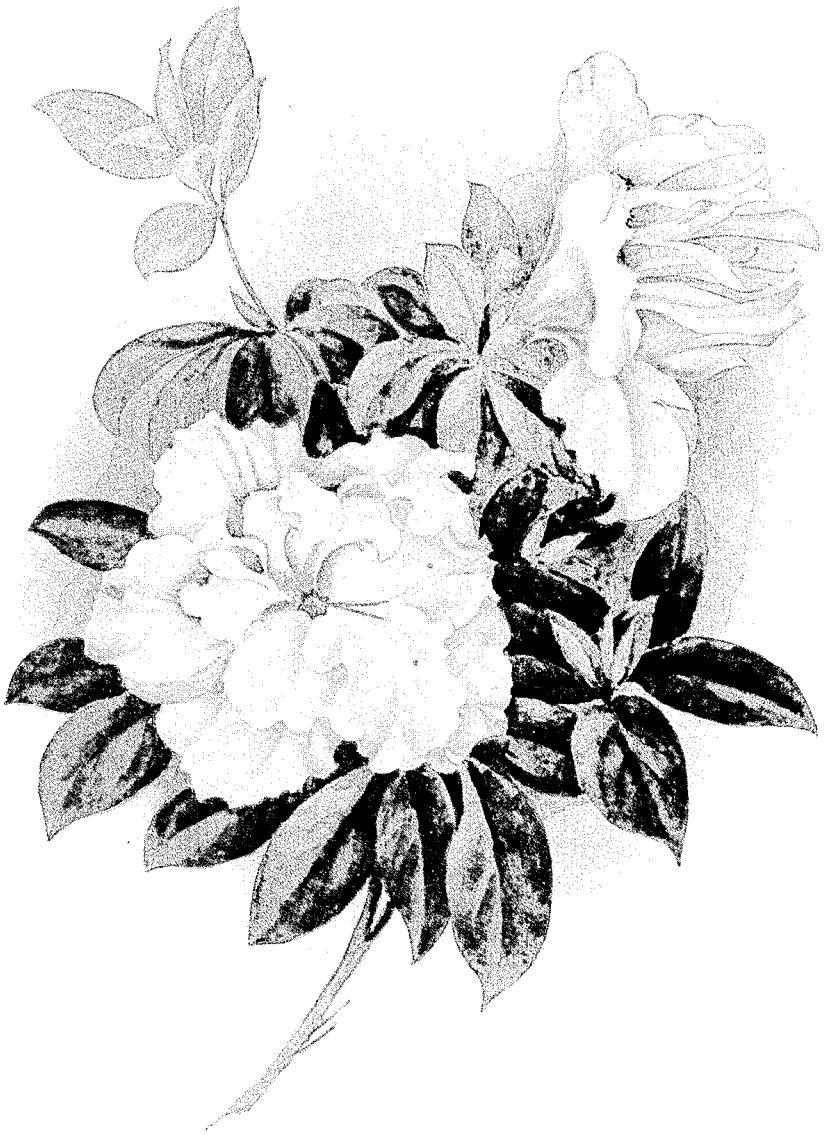
WITNESS
Addison E. Avery
INVENTOR
LENARD L. BROOKS
Webster & Webster
ATTYS.

Patented Dec. 23, 1952

Plant Pat. 1,157

UNITED STATES PATENT OFFICE 1,157

AZALEA PLANT

Lenard L. Brooks, Modesto, Calif.

Application January 28, 1952, Serial No. 268,603

1 Claim. (Cl. 47—60)

This invention is directed to a new and distinct variety of azalea plant, such plant being principally characterized by its large double white flowers marked with pink; its ease of reproduction on its own roots; its high value as a greenhouse forcing or garden variety; its rapid yet much branched compact habit of growth; and its large glossy green leaves.

The variety is a cross produced in the experimental garden of my nursery at Modesto, California; the cross having been made by pollen from the Kurume azalea Hexe used on the Belgian Indica azalea Pink Pearl; neither of the parent varieties being patented.

The cross as produced above was immediately recognized by me as having substantial novel characteristics and evidenced high possibility for commercial use. It was therefore taken for propagation by cuttings, and the first cuttings produced azalea plants which carried forward all of the distinguishing features of the parent.

The original asexual reproduction of the variety by cuttings was carried out in my experimental garden located as aforesaid. Subsequent propagations of the variety by cuttings further evidences that the variety is fixed in its floricultural characteristics.

The figure of the drawings is a perspective view of twigs with leaves and flowers; the leaves and flowers being of the color when the plant is grown outdoors.

Referring now more specifically to the botanical details of this new and distinct variety of azalea plant, the following is an outline description thereof; all major color plate identifications being by reference to Maerz and Paul Dictionary of Color.

*Plant*

Form: Well branched, symmetrical form. The height and breadth of the young plants are usually about the same, but as the plants age, the breadth gradually becomes greater.

Growing habit: Dense and bushy with an abundance of large medium green leaves with good texture and weight. It grows very rapidly, often attaining a spread of three feet in four years from the rooted cutting. A minimum of pruning is required to produce well shaped plants.

Blooming habit: Very profuse, flowering evenly over the entire plant at the same time, whether forced in the greenhouse or flowered naturally in the garden. It flowers profusely as a one-year plant. It produces from one to four flowers on each stem.

Blooming season: March-April in central California. It is very easily forced into flower out of season in the greenhouse. If grown properly, it is easily forced for Christmas.

Foliage:

*Size.*—Mature leaves average 1½″ to 2½″ in length, and ¾″ to 1¼″ in width.

*Color.*—On outdoor grown plants: New leaves, light yellow-green (20–L–6); mature leaves, medium green (23–L–6); under side, lighter green. On greenhouse grown plants: The color of the mature leaves becomes a somewhat deeper green (23–H–6, shading to 23–L–8); under side, lighter green.

*Shape.*—Ovate, pointed.

*Aspect.*—Glossy and smooth.

*Texture.*—Medium. It is a lighter textured leaf than many of the Indica azaleas. It is similar to the leaf of the well known Kurume azalea Salmon Queen. The quality is excellent, which is established by the fact that it starts very easily from cuttings.

*Edge.*—Smooth.

*Ribs and veins.*—Normal.

Stems of foliage:

*Color.*—Main stem, greyish brown (5–B–7) with smaller or side stems darkening to 7–H–10.

Flower:

*Size.*—Average 3″ to 4¾″ in diameter.

*Borne.*—One to four on each stem.

*Stem.*—Medium length; strong.

*Form.*—Commonly known as double. The flower consists of a single hose or trumpet as found in a single azalea flower, except that the flower opens wider, and the petals are more reflexed, with a varying number of small petals or petaloids in the center. These petaloids are often antheriferous, usually standing quite erect rather than lying close to the outer trumpet as in hose in hose azalea flowers. The flower has a depth according to the length of the petaloids, which are often substantially the length of the outer petals. At times the flowers take nearly the form of a hose in hose azalea flower, although this variety has never been known to develop into a perfect hose in hose form.

*Permanence.*—Long lasting, retaining its beauty until the flowers are ready to fall.

*Petalage.*—Five reflexed petals on the outer flower, with the center of the flower composed of a varying number of petaloids; the latter being rarely more than seven and these are often antheriferous. Both the outer flower and petaloids are slightly ruffled. Rarely do the latter develop anthers when the maximum size is reached. The development of anthers has a direct effect on the size and shape of the petaloids; the anthers having a dwarfing and distorting effect, thus causing considerable variation in the center structure of the flower.

*Color.*—The basic color is pure white, with yellow green markings in the upper portion of the throat; such markings on newly opened flowers being stronger green (17–L–8), but as the flowers age, such color lightens to 17–L–7—17–L–4. The entire flower is marked by dashes, stripes, or dots of pink (41–J–2—41–J–3); such pink color markings being of various sizes that will at times embrace half a petal, an entire petal, or—rarely—the entire flower. Where large markings occur they will often carry secondary markings in a deeper shade of pink.

*Petals.*—Texture — substantial. Appearance—velvety, inside and out, reflexed. Size—average 1¼'' to 1¾'' wide and 1½'' to 2¼'' long. Shape—ovate, narrowing abruptly at lower end. Arrangement—normal Indica type. Persistence—remains firm without wilting until flower is ready to fall.

Reproductive organs:

*Stamens.*—Stamens do not usually occur in this variety, but if the number of petaloids decrease, some stamens may develop, usually only one or two. Anthers often develop on the petaloids and when this occurs, the petaloids become dwarfed and distorted. Anther creamy-white, brownish with age. Filament—when it occurs—white.

*Pollen.*—White.

*Style.*—White, rarely pinkish. The length varies, but is often 1¾''. Stigma about the color of the throat markings. Both style and stigma usually well developed.

*Ovaries.*—Normal.

*Comparison*

As compared to other and well known varieties of azalea plants, the instant variety somewhat resembles the Indica variety of azalea Pink Pearl, the pollen parent, but with the following differences:

1. The flowers are larger.
2. The petaloids are usually larger, longer, and stand more erect.
3. The colors are widely different; the Pink Pearl azalea being a delicate pink throughout, while the present variety, as aforesaid, is basically pure white splashed with pink.
4. It has the blooming habit of the Kurume azaleas; i. e. it comes into flower evenly over the entire plant rather than over a longer period with a few flowers at a time, as is the habit of the Belgian Indica azaleas.
5. It has a thinner textured foliage.
6. It starts easier from cuttings, grows faster, and branches better, with a more compact habit of growth, therefore producing more flowers.

Tests indicate that the present variety of azalea plant is hardier and easier to grow than most Indica varieties of azalea plants.

To my knowledge there is no known azalea plant having a flower comparable to the flower of the present variety.

The plant and its flower herein described may vary in slight detail due to climatic and soil conditions under which the variety may be grown. For example, foliage color of an azalea is closely related to the conditions under which the plant is grown and the amount of acid used in its culture, and such color can thus vary substantially.

Having thus described the invention, I claim:

A new and distinct variety of azalea plant of the Indica class comprised of a cross between the Kurume azalea Hexe and the Belgian Indica azalea Pink Pearl; characterized by large double white flowers marked or splashed with pink, which flowers include long large petaloids which stand erect, which petaloids tend to dwarf and distort when anthers exist; and the plant being easy of reproduction on its own roots; being excellent as a greenhouse forcing variety; and having rapid yet much branched compact habit of growth, with large glossy green leaves.

LENARD L. BROOKS.

No references cited.